United States Patent [19]

Berg et al.

[11] Patent Number: 4,837,285

[45] Date of Patent: Jun. 6, 1989

[54] COLLAGEN MATRIX BEADS FOR SOFT TISSUE REPAIR

[75] Inventors: Richard A. Berg, Lambertville, N.J.; Frederick H. Silver, Bangor, Pa.; James M. Pachence, Lawrenceville, N.J.

[73] Assignee: MediMatrix, Princeton, N.J.

[21] Appl. No.: 93,826

[22] Filed: Sep. 8, 1987

Related U.S. Application Data

[63] Continuation-in-part of Ser. No. 875,827, Jun. 18, 1986, which is a continuation-in-part of Ser. No. 843,828, Mar. 26, 1986, Pat. No. 4,703,108, which is a continuation of Ser. No. 593,733, Mar. 27, 1984, abandoned.

[51] Int. Cl.$^4$ ............ C08H 1/06; A23J 1/10; A61K 37/02
[52] U.S. Cl. .................. 530/356; 523/105; 524/21; 128/156; 128/DIG. 8
[58] Field of Search ............. 530/356; 128/DIG. 8, 128/156; 524/17, 21; 527/201; 523/105

[56] References Cited

U.S. PATENT DOCUMENTS

| | | | |
|---|---|---|---|
| 3,098,693 | 7/1963 | Sheehan | 106/122 |
| 3,300,470 | 1/1967 | Young | 530/354 |
| 3,800,792 | 4/1974 | McKnight | 128/156 |
| 3,903,882 | 9/1975 | August | 128/155 |
| 3,955,012 | 5/1976 | Okamura | 427/2 |
| 4,060,081 | 11/1977 | Yannas et al. | 128/156 |
| 4,280,954 | 7/1981 | Yannas | 530/356 |
| 4,350,629 | 9/1982 | Yannas | 530/356 |
| 4,352,883 | 10/1982 | Lim | 435/178 |
| 4,363,758 | 12/1982 | Masuho et al. | 424/85 |
| 4,374,121 | 2/1983 | Cioca | 530/356 |
| 4,399,123 | 8/1983 | Oliver | 424/95 |
| 4,409,332 | 10/1983 | Jefferies et al. | 530/356 |
| 4,412,947 | 11/1983 | Cioca | 106/124 |
| 4,418,691 | 12/1983 | Yannas | 128/156.3 |
| 4,424,208 | 1/1984 | Wallace et al. | 530/356 |
| 4,458,678 | 7/1984 | Yannas | 128/155 |
| 4,522,753 | 6/1985 | Yannas et al. | 530/356 |
| 4,703,108 | 10/1987 | Silver et al. | 523/111 |

FOREIGN PATENT DOCUMENTS 2734503 2/1979 Fed. Rep. of Germany.

OTHER PUBLICATIONS

Doillen et al, Scanning Electron Microscopy, 1985, pp. 897–903.
Silver et al, J. Biomed. Mat. Res., vol. 13, 701–715 (1979).
Silver et al, Throm. Res., vol. 13, pp. 267–277 (1978).
Weadock et al, Biomat. Med. Dev., Art. Org., 11(4), 293–318 (1983–84).
Chem. Abstracts, 82:744856, 1975.
Ruben et al, J. Clin. Pharm., pp. 309–312 (1973).
Chem. and Eng. News, Oct. 4, 1965.

*Primary Examiner*—John Kight
*Assistant Examiner*—Nathan M. Nutter
*Attorney, Agent, or Firm*—Michael Ebert

[57] ABSTRACT

Collagen-based compositions for augmenting soft tissue, wound dressings, implants, injectable formulations or other drug delivery systems, comprising resorbable collagen matrix beads, the beads having an average pore size of from 50 to 350 microns, and the collagen comprising from 1 to 30% by volume of the beads, the collagen matrix being sufficiently open to stimulate cellular ingrowth therethrough and yet sufficiently stiff and non-compressible to fill and protect a wound, and the formulation being sufficiently moisture and gas permeable to prevent liquid pooling on a wound and to permit sufficient oxygen diffusion for promoting wound healing.

15 Claims, No Drawings

COLLAGEN MATRIX BEADS FOR SOFT TISSUE REPAIR

CROSS-REFERENCE TO RELATED APPLICATIONS

This application is a continuation-in-part of copending application Ser. No. 875,827 filed June 18 ,1986;which was a continuation -in-part of application Ser. No. 843,828 filed Mar. 26, 1986 and now U.S. Pat. No. 4,703,108; which application was in turn a continuation of application Ser. No. 593,733 filed Mar. 27, 1984, now abandoned.

BACKGROUND OF THE INVENTION

1. Field of the Invention

This invention relates to a collagen-based composition for augmenting soft tissue repair, a collagen-based wound dressing and a collagen-based drug delivery system.

2. Background of the Invention

Collagen is the major connective tissue protein in animals. It has an extended history of use in the medical field primarily due to its ability to polymerize in vitro into strong fibers that can be fabricated into a number of forms. Collagen has been utilized for a variety of clinical purposes including wound treatment, hemostasis, and soft tissue augmentation. We have described these and other medical applications of collagen in a recent review. Pachence J. M., Berg R. A., and Silver F. H., "Collagen: Its Place in the Medical Device Industry", Med. Device & Diag. Ind., 9:49–55, 1987.

Soluble collagen has been used as a subcutaneous implant for repairing dermatological defects such as acne scars, glabellar furrows, excision scars and other soft tissue defects. Klein, A. W. J.Acad. Derm. 9:224–228 (1983); Knapp, T. R., Luck, E., and Daniels, J. R. J.Surg. Res. 23:96–105 (1977); and Kaplan, E. N., Falces, E., and Tolleth, H. Clinical Utilization of Injectable Collagen, Ann. Plast. Surg., 10:437–451 (1983). Although it appers that this implant is readily accepted, the repair of the defects is temporary and patients need additional treatment after 6 to 18 months. There were also a number of adverse tissue responses after utilization of soluble collagen. Castrow, F. F., and Krull, E. A. Injectable Collagen Implant—Update, J. Am. Acad. Dermatol. 9:889–893 (1983). Labow, T. A., and Silvers, D. N. Late Reactions at Zydern Skin Test Sites, Cutis 35:154—158 (1984) and Cohen, I. K. Peacock, E. E., and Chvapil, M. Editorial on Zyderm, Plast. Reconstr. Surg., 73:1 (1984).

Collagen has also been used in many forms as a wound dressing. The various forms of collagen wound dressings include collagen sponges such as described in Artandl U.S. Pat. No. 3,157,524 and Berg et al U.S. Pat. No. 4,320,201; and collagen/polymer film composites such as described in McKnight et al, U.S. Pat. No. 3,800,792. However, many of these dressings are not satisfactory for the various types of full thickness wounds. Collagen films and sponges do not readily conform to varied wound shapes. Further, some collagen wound dressings such as collagen films have poor fluid absorption properties and enhance the pooling of wound fluids.

The use of Type I collagen in a wound dressing has had limited success due to its reported limited application for epidermal cell support. It has been indicated that attachment factors such as laminin and Type IV collagen are necessary for optimal epidermal cell growth. Lillie, J .H., MacCullum, D. K., and Jepsen, A. In: *Epithelial Messenchymal Interactions in Development*, R. H. Sawyer and J. F. Fallon, eds., Praeger Scientific, N.Y. 1983, pp 99–111; Stanley, J. R. Foidart, J., Murray, J. C. Martin, G. D. and Katz, S. T. (1980) J. Invest. Dermatol. 74:54–58; and Kleinman, H. K., Klebe, R. J., and Martin, G. R. The Role of Collagen Matrices in Adhesion and Growth of Cell., J. Cell Biol. 88:473 (1981). Similarly, the presence of hyaluronic acid or fibronectin greatly improves the ability of the matrix to support fibroblast growth. (Doillon et al. (1987) Biomaterials 7:195–200).

It is, accordingly, among the objects of the present invention to provide an improved collagen-based wound dressing, and a method for augmenting soft tissue repair therewith.

SUMMARY OF THE INVENTION

In accordance with the present invention a wound dressing and composition for soft tissue repair is provided comprising completely resorbable collagen matrix beads having an average pore size of about 50 to 350 microns, with the collagen comprising up to about 10% by volume of the beads. In particular, the collagen matrix is sufficiently open to stimulate cellular ingrowth therethrough and yet sufficiently stiff and non-compressible to fill and protect a wound or to conform to tissue to be repaired, and is sufficiently moisture and gas permeable to prevent liquid pooling on a wound and to permit sufficient oxygen diffusion for promoting wound healing and tissue growth.

The formulations of the invention provide tissue ingrowth through cell migration into the interstices of the collagen matrix. The very porous collagen matrix forms a skeleton providing sufficient volume for cells to attach and grow into the matrix, and to synthesize their own macromolecules. The cells thereby produce a new matrix which allows for the growth of new tissue. Such cell development is not observed on other known forms of collagen such as fibers, fleeces and soluble collagen.

A further advantage of the wound dressing and composition for soft tissue augmentation of the present invention is its ability to conform to varied sizes and shapes of wounds. Many wounds, due to their odd sizes and shapes are not conducive to sponge or film dressings.

An additional advantage of the collagen bead formulations hereof over collagen sponges and films is the ability of the beads to be administered in injectable form. A subcutaneous injection of collagen promotes the development of cells throughout the depth of the wound area, not solely on the surface of the implant.

The rate of wound healing is further enhanced by the addition to the collagen bead formulation of a macromolecule capable of promoting tissue ingrowth, such as hyaluronic acid or fibronectin. Doillon et al. (1987) Biomaterials 8:195–200; and Doillon and Silver (1986) Biomaterials 7:3–8. Hyaluronic acid in the collagen matrix encourages cellular infiltration into the pores and channels of the matrix. Fibronectin induces cell attachment to the collagen fibers of the matrix. Thus, incorporation of hyaluronic acid and/or fibronectin into the collagen bead composition enhances cell mobility and replication in the collagen matrix, and promotes cell ingrowth into the wounds or defective tissues treated therewith. Other macromolecules such as collagen types IV and V, laminin, and proteoglycans can also be added to the matrix to alter cell growth.

Another advantage of the present invention is the incorporation into and the subsequent delivery from the collagen matrix beads of pharmacological agents such as platelet-derived growth factor, epidermal growth factor, transforming growth factor beta, angeogenesis factor, antibiotics, antifungal agents, spermicidal agents, hormones, enzymes, or enzyme inhibitors.

DETAILED DESCRIPTION

The collagen matrix beads employed in the wound dressing and soft tissue repair compositions, of the invention are constituted of a native Type I or Type III collagen which is free of foreign materials and completely resorbable by a patient's body. The collagen is in the form of a crosslinked material having a molecular weight of about $1 \times 10^6$ to $50 \times 10_6$ or more, the collagen between adjacent crosslinks having a molecular weight of about 1,000 to 100,000. For the purposes of the present invention, the collagen matrix is in the form of discrete, porous beads having particle sizes of from about 100 to 4000 microns, preferably about 300 to 500 microns, and porosities such that the collagenous material comprises up to about 30%, and generally about 1 to 30% (most desirably about 2 to 5%), of the total bead volume.

The collagen matrix defining the bead structure is in the form of a network of fine fibers having thicknesses varying from about 5 to 35 microns, preferably about 10 microns. The fibers define surface and interior pores connected by internal channels, the average pore size being about 50 to 350 microns, preferably $100 \pm 50$ microns. Such matrix is sufficiently open as to stimulate cellular ingrowth therethrough yet sufficiently stiff and non-compressible as to fill and protect a wound. Desirably, the matrix has a stiffness of at least $10^3$, and preferably about $10^4$ to $10^5$, Newtons $(N)/m^2$. The collagen matrix beads hereof also absorb 10 to 50 times their weight of liquid and expand 3 to 5 times in volume, thus preventing liquid pooling in the wound bed.

The collagen matrix beads are suitably prepared by dispersing an appropriate Type I or Type III collagen in an appropriate solvent or diluent, forming the dispersion into minute droplets, freezing the droplets, and forming the droplets into porous beads, by lyophilization. The collagen material is then crosslinked into a permanent matrix, employing biologically inert, non-toxic crosslinking agents. More particularly, the collagen dispersion is prepared employing the techniques described, for example, in the aforesaid parent U.S. patent applications Ser. Nos. 593,733; 843,828; and 875,827. The collagen is dispersed in lower aliphatic monocarboxylic acids (such as formic, acetic, or propionic acid), or in dilute HCl, with the dispersion having a collagen to liquid weight ratio fo 1:10,000 to 1:10. The collagen dispersion is admixed wtih other adjuvants at this point (e.g., type II or IV collagen, hyaluronic acid, fibronectin, other growth factors or the like). The dispersion is degassed under low pressure (0.5 to 0.01 Torr) until gas bubbles no longer appear. The pH of the dispersion is adjusted to between pH 2 and 5, preferably about pH 3.0.

Droplets having sizes ranging from about 0.05 mm to 4.0 mm are thereafter formed, suitably in a manner similar to that described by Dean, et al. in PCT Publication WO No. 86/05811, "Weighted Microsponge for Immobilizing Bioactive Material," taking care to exclude foreign materials of the type utilized as weighing additives in the microsponge cell substrates thereof. Suitable techniques include spray drying, emulsification, extrusion, electrostatic droplet formation, and others.

The dispersion droplets can be sprayed into a cooled organic solvent bath that is immiscible with water (e.g., hexane, chloroform or methanol) at less that $-20°$ C. but above the freezing point of the organic solvent in order to freeze the droplets. The diameter of the aperture used to form the dispersion droplets determines the size of the particles. Alternatively, the dispersion droplets can be sprayed into liquified gas (such as liquid nitrogen), to freeze the droplets. The frozen droplets are placed directly into pre-cooled drying trays, and lyophilized in order to form the microporous beads; vacuum is maintained at below 0.1 mtorr, and the temperature is gradually brought from $-60°$ to $20°$ C. over a 48 hr. period.

Alternatively, the collagen droplets are sprayed into an organic solvent bath maintained at less than $-20°$ C.; the bath contains an agent which crosslinks the collagen. The frozen collagen droplets are removed from the solvent, and air dried while gradually raising the temperature.

Once the microporous beads have formed, additional crosslinking is desirably effected. In accordance with the present invention, it is essential that the collagen matrix beads incorporated in the medicinal formulations hereof be high purity native materials, free of potentially toxic additives which may impair tissue ingrowth or preclude complete resorption upon topical application, implantation or subcutaneous injection into patients. Consistent therewith, crosslinking of the collagen matrix beads can be effected by dispersing the beads in a solution of a carbodiimide (such as cyanamide or 1-ethyl-3-(3-dimethylamino-propyl)-carbodiimide hydrochloride), or a bifunctional N-hydroxy succinimide-derived ester (such as bis(sulfosuccinimidyl) suberate). The chemical crosslinking may be used in combination with severe dehydration at temperatures between $50°$ C. and $200°$ C. in a vacuum of less than 50 torr for 2 to 92 hours. Such techniques have been described in detail in the aforesaid parent U.S. patent applications Ser. Nos. 593,733; 843,828; and 875,827.

The collagen matrix beads are incorporated in wound dressings or implants in the form of a dry powder or in a pharmaceutically acceptable, inert carrier. The carrier can be a non-toxic base for forming an ointment, gel, gel cream or cream incorporating the matrix beads such as, for example, petrolatum, propylene glycol, isopropyl myristate, or lanolin (for ointments); petrolatum or gelatin (for gels); or mono- and di-glycerides, ester waxes, or stearyl alcohol (for creams).

Macromolecules such as hyaluronic acid, fibronectin, collagen types IV and V, laminin, and protoglycans will affect cell growth when incorporated into the collagen matrix beads. Thus, the above mentioned macromolecules may be added to the collagen dispersion, prior to formation of the matrix beads, in amounts of about 0.01 to 2.0% by volume of the dispersion.

Pharmacologically active agents such as platelet-derived growth factor, epidermal growth factor, transforming growth factor beta, angeogenesis factor, antibiotics, antifungal agents, spermicidal agents, hormones, enzymes, or enzyme inhibitors can also be incorporated in the collagen matrix and subsequently delivered to the tissue. The above mentioned agents are added to the collagen dispersion, prior to formation of the matrix beads, in amounts varying, for example, from about 1.0 ng/ml to 0.1 mg/ml for the growth factors, and 0.001 mg/ml to 10 mg/ml for hormones, enzymes, and enzyme inhibitors. The chemical crosslinking and the pore size of the collagen matrix are altered in order to alter the delivery dose of these agents from the collagen matrix beads, so that 90% of the agent is delivered from the matrix in from 1 to 72 hours.

Wound dressings comprising such compositions are completely resorbed by the patient's body within about 2 to 30 days, preferably within ten days.

When employed in subcutaneously injectable formulations for soft tissue augmentation, the collagen matrix beads are suitably dispersed in a sterile aqueous dispersion in water containing physiological salts, or in a non-aqueous dispersing agent such as glycerol, liquid polyethylene glycol, vegetable oils, animal oils, mineral oils, or mixtures thereof. In order to improve the flow characteristics of the injectable dispersion, hyaluronic acid in the amount of 0.1 to 5% in physiological saline is used to disperse the beads. Such formulations must be fluid to the extent necessary to provide easy syringeability (through 15 to 30 gauge needles), stable under the conditions of manufacture and storage, and preserved against the contaminating action of microorganisms such as bacteria or fungi.

The proper fluidity of the injectable formulations can be maintained by the addition of a surfactant, hydroxypropyl cellulose, fatty acids or bile acids, to the dispersion in amounts of about 0.01 to 1.0% by weight thereof. Prevention of the action of microorganisms can be insured by the addition of various anti-bacterial and anti-fungal agents, e.g., paraben, chlorobutanol, phenol, sorbic acid, thimerosal, or the like, in amounts of about 0.001 to 0.5% of the formulation. It may also be desirable to incorporate isotonic agents, e.g., sugars or sodium chloride, in amounts of about 0.1 to 1.5%, in the injectable composition. Prolonged absorption can also be achieved by incorporating absorption-delaying agents, e.g., aluminum monostearate or gelatin, in amounts of about 0.01 to 1.0%.

Preferably, and as noted hereinabove, the wound dressings, implants and injectable formulations of the invention additionally contain a macromolecular material for promoting tissue ingrowth such as hyaluronic acid or fibronectin (see "Fibroblast Growth on a Porous Collagen Sponge containing Hyaluronic Acid or Fibronectin, Doillon, C. J.; Silver, F. H. and Berg. R. A., Biomaterials 8:195-200), or mixtures thereof. It is believed that these materials, or other tissue growth-stimulating factors, e.g., transforming growth factor beta (see Raghaw, R., Postlethwaite, A. E., Keski-Oja, J., Moses, H. L., and Kang, A. H. (1987) 79:1285-1288) or platelet-derived growth factor (Sato, G. H., Ross, R. eds. Hormones and Cell Culture, Books A and B, New York, Cold Spring Harbor), in admixture with the collagen matrix beads, promote fibroblast synthesis of extracellular matrix material (TGFB) or stimulate cell division (PDGF).

The specific nature of the compositions of the present invention will be more fully apparent from consideration of the following specific examples of preferred embodiments thereof. In the examples, as in the preceding description, all parts and percentages are given by weight unless otherwise indicated.

EXAMPLES

Example 1

Collagen I Material Utilized in the Preparation of the Matrix Beads

In the following preparation, the insoluble collagen fraction was isolated from deep flexor tendons of cattle.

Freshly harvested bovine tendon which had been kept in cold buffer was thoroughly washed and cleaned; sodium lauryl sulfate was used to help remove the gross contaminants such as hair, fat, non-fibrous membranes, and other foreign matter. Before storage, the tendons were thoroughly rinsed with deionized distilled water. The cleaned tendons were stored at $-5°$ C. The tendons were thinly sliced using a commercial processor, with the thickness of slices being approx. 1 mm.

The slices were then treated with a proteolytic enzyme used to remove elastin, fat, other non-collagenous materials. The reaction was carried out at 37° C., pH 6.15, in 20 mM phosphate buffer; the dry weight ratio of protein to enzyme was 5. The slices were agitated for 4 hours; immediately thereafter, floating debris was skimmed from the top of the vessel. The temperature was slowly brought to 25° C., and a solution of 1% ammonium nitrate and 0.1% sodium chloride was added to inactivate the enzyme. The slices were washed thoroughly, then allowed to drain overnight at 5° C.

The thus treated slices were dispersed in an organic acid (e.g., 1% acetic acid) in which the fibrillar mass was allowed to undergo controlled swelling, followed by homogenization and filtration. Further purification was effected by precipitating non-collagenous material with solutions of gradually increasing concentrations of ammonium sulfate. The collagen dispersion was then precipitated at pH 4.5, then washed thoroughly, redispersed in 1% acetic acid, and homogenized.

The thus purified collagen is converted to collagen matrix beads as described in the following further examples.

Example 2

Preparation of Collagen Matrix Beads Employing Chemical Crosslinking

A. Formation of Beads

A 1.2 gm sample of insoluble collagen is suspended in 120 ml of 0.001 N HCl and the pH is adjusted to 3.0. The sample is then blended in a blender at high speed for 3 min. The dispersion is placed in a container and degassed at a reduced pressure of 10 millitorr until air bubbles are removed. The dispersion is then flowed through a vibrating, hollow tube having a diameter of 0.1 to 1.5 mm where droplets are allowed to drop into a cryogenic bath of liquid $N_2$ where they freeze. After allowing the $N_2$ to evaporate, the still frozen beads are transferred to a lyophilizer where the frozen water is removed at a vacuum of about 10 millitorr until the beads have less than 0.1% moisture.

B. Crosslinking the Beads

The thus formed beads are crosslinked by immersion in an aqueous solution containing 1% by weight of cyanamide at pH 5.5 for 24 hrs. at 22° C.. After removal the beads are washed in a sintered glass funnel with 10 volumes of $H_2O$ frozen in a metal tray and re-lyophilized at $-40°$ C. in a vacuum of less than 50 millitorrs. The beads are then air dried at a temperature of from 10 to 100° C. under reduced pressure of less than 50 millitorr.

Example 3

Preparation of Collagen Matrix Beads Employing Heat Crosslinking

The beads formed as described in Example 2(A) are crosslinked by being placed in a vacuum oven at room temperature and exposed to a vacuum of less than 50 millitorr for 1 hr. The temperature is thereafter raised to 100° C. for 72 hr., after which it is lowered to 20° C. The samples are removed from the oven and stored at −20° C. to +20° C.

The samples may be sealed into plastic bags that limit air diffusion and prevent contamination. The samples are sterilized by exposure to 2.5 M rads of gamma radiation from a $^{60}$Co source or x-rays.

Example 4

Preparation of Collagen Matrix Beads Employing Chemical and Heat Crosslinking The crosslinked beads prepared as described in Example 2 are further subjected to heat crosslinking as set out in Example 3.

Example 5

Preparation of Collagen Matrix Beads Having Varying Swelling Ratios

The swelling ratios of the crosslinked collagen beads produced by the above procedures are determined by boiling the beads for 2 minutes in distilled water and thereafter blotting them dry.

The sample is weighed and the weight recorded. The sample is then dried at 100° C. for 3 hrs. and reweighed. The swelling ratio is calculated as follows:

$$r = 1/V_f \text{ where } V_f = \frac{DW/PC}{\frac{DW}{PC} + \frac{WW - DW}{P_{water}}}$$

where DW and WW are the dry and wet weights of the sample, and PC and $P_{water}$ are the densities of the sample and water.

The swelling ratios are inversely proportional to the degree of crosslinking, which latter may be regulated by choice of the crosslinking conditions (e.g., the concentrations of the crosslinkers). For example, by crosslinking the beads with cyanamide for 24 hrs. in the manner described in Example 1, collagen matrices having swelling ratios of approximately 5 to 10 are obtained. Using the dehydrothermal method described in Example 3, swelling ratios of 3 to 5 are obtained.

Example 6

Preparation of Collagen Matrix Beads Containing Hyaluronic Acid

To the dispersion formed in Example 2(A) is added 5% hyaluronic acid w/w collagen. The dispersion is adjusted to pH 3.0 and beads are formed as described in Example 2(A).

A collagen matrix containing this formulation of hyaluronic acid significantly promotes the growth of fibroblasts as compared with the collagen matrix alone (Doillon et al (1987) Biomaterials 8:195-200). Such a matrix also enhances wound healing in guinea pigs (Doillon and Silver (1986) Biomaterials 7:3-8).

Example 7

Preparation of Collagen Matrix Beads Containing Fibronectin

A preparation containing 1% fibronectin w/w collagen is made by adding 12 mg fibronectin to 1.2 gms insoluble collagen and dispersing the mixture in HCl as described in Example 2(A). The dispersion is adjusted to pH 3.0 and beads are formed as further described in Example 2.

A collagen matrix containing this formulation of fibronectin promotes significantly greater growth of fibroblasts than the collagen matrix alone (Doillon et al (1987) Biomaterials 8:195-200). A matrix containing fibronectin also promotes wound healing in guinea pigs (Doillon and Silver (1986) Biomaterials 7:3-8).

Example 8

Wound Dressing Containing Collagen Matrix Beads

In this example, a full and partial thickness wound is treated with dry, sterile collagen matrix beads.

The collagen matrix beads prepared as described in any of Examples 2-7, packaged in an airtight container, are sterilized by 2.4 mRad gamma irradiation for 2 hours. The collagen beads are distributed evenly over the wound bed, placing about 0.5 gram of material over a 2 sq. in. area. When the collagen beads have absorbed about 80% of their capacity from the wound exudate, the beads are washed out of the wound and fresh beads are applied. The collagen beads can remain in the wound, as they will reabsorb within 14 days.

Example 9

Wound Dressing Containing Collagen Matrix Beads in a Sterile Paste

In this example, a full or partial thickness wound is treated with a sterile paste containing the collagen matrix beads.

The collagen matrix beads as described in any of Examples 2-7, are mixed into a paste containing 1% propylene glycol, 5% gelatin, and 10% collagen. This mixture is packaged in an air-tight plastic tube, and sterilized by 2.4 mRad gamma irradiation for 2 hours. The paste is distributed evenly over the wound bed, placing about 20 cc of material over a 2 sq. in. area. The paste/collagen bead material can remain in the wound, which will be reabsorbed by the wound with 14 days.

Example 10

Injectable Solution Containing Collagen Matrix Beads

The collagen matrix beads, prepared as described in any of Example 2-7, are mixed with a solution containing 2% glycerol, 0.9% sodium chloride, and 10 mM sodium phosphate at pH 7.2. This collagen dispersion is placed in a 1 cc syringe having a 28 gauge needle; the apparatus is packaged in a bacteriostatic plastic bag, and then sterilized. The sterile collagen dispersion is then delivered via subcutaneous or cutaneous injection to augment soft tissue. Fibroblasts ingrow and populate the matrix; the collagen matrix beads are remodelled and replaced by native collagen within 36days.

Example 11

Antibiotic-Containing Collagen Matrix Beads

Pharmacologically active ingredients are incorporated in the collagen dispersion formed in Example 2(A), prior to the formation of the matrix beads. The antibiotic silver sulfadiazine is added to the dispersion at a concentration of 1%; the collagen dispersion containing the antibiotic, is then formed into matrix beads as described above.

Example 12

Succinylated Collagen Matrix Beads

Succinylated collagen is prepared, and is used in the collagen matrix bead formulation of Example 2.

Nine grams of succinic anhydride are dissolved in 80 ml of pure water, and mixed for 30 minutes at 37° C.; the pH is adjusted to 7.2, and the volume brought to 100 ml. This solution is placed in a blender, and 1 gram of collagen is added. The mixture is blended for 2 minutes and allowed to stand at 22° for 1 hour. The collagen is water-washed over filter paper with 10% volume.

Succinylated collagen binds ions such as silver more efficiently, to facilitate drug delivery. Succinylated collagen also can also be used to modify cell growth properties.

From the preceding, it will be seen that, in accordance with the present invention, an improved class of collagen-containing wound dressings, growth-promoting implants and injectable formulations is provided. It will be understood that various changes may be made in the mode of preparation and formulation of the compositions of the invention without departing from the scope thereof. Accordingly, the preceding disclosure should be construed as illustrative only, the scope of the invention to be interpreted in accordance with the claims appended hereto.

What is claimed is:

1. A wound dressing or implant comprising resorbable, porous collagen matrix beads having particle sizes of from about 100 to 4000 microns, the beads having an average pore size of from about 50 to 350 microns, and the collagen comprising from 1 to 30% by volume of the beads, the porous collagen matrix forming a skeleton providing a volume sufficient for cells to attach and grow into the matrix and being stiff and non-compressible to a degree sufficient to fill and protect a wound, the dressing or implant having a degree of moisture and gas permeability sufficient to prevent liquid pooling on a wound and to permit sufficient oxygen diffusion for promoting wound healing.

2. The wound dressing of claim 1 wherein the collagen matrix beads are prepared from Type I or Type III collagen.

3. The wound dressing of claim 1 wherein the collagen matrix beads are in the form of a dry powder.

4. The wound dressing of claim 1 wherein the collagen matrix has a pore volume of from 80 to 99% by volume, and the matrix is constituted of fibers having a thickness of from 5 to 35 microns and has a stiffness of from $10^3$ N/m$^2$ to $10^5$ N/m$^2$.

5. The wound dressing of claim 1 further comprising a macromolecule for promoting tissue ingrowth.

6. The wound dressing of claim 5 wherein the macromolecule is hyaluronic acid or fibronectin, or mixtures thereof.

7. The wound dressing of claim 5, wherein the macromolecule is transforming growth factor beta, platelet-derived growth factor, or a mixture thereof.

8. A compostion for injection into a wound site in mammals for promoting soft tissue augmentation, comprising a suspension of resorbable, porous native collagen matrix beads having particle sizes of about 100 to 4000 microns in an aqueous medium, the beads having an average pore size of 50 to 350 microns, the collagen comprising from 1 to 30% by volume of the beads, the porous collagen matrix beads forming a skeleton providing a volume sufficient for cells to attach and grow into the matrix, and being stiff and non-compressible to a degree sufficient to conform to the tissue to be repaired.

9. The composition of claim 8, wherein the suspension comprises the collagen matrix beads in an aqueous solution of a macromolecule for promoting tissue ingrowth.

10. The composition of claim 8, wherein the suspension comprises collagen matrix beads in admixture with an aqueous solution of transforming growth factor beta, platelet-derived growth factor, hyaluronic acid, fibronectin or mixtures thereof.

11. The composition of claim 8, wherein the collagen matrix has a pore volume of from 80 to 99% by volume, and the matrix is constituted of fibers having a thickness of from 5 to 35 microns and has a stiffness of from $10^3$ to $10^5$ N/m$^2$.

12. A method for augmenting wound healing or soft tissue repair in mammals, comprising topically applying or implanting the composition of claim 1.

13. A method for augmenting soft tissue repair in mammals, comprising injecting the composition of claim 8 subcutaneously into a patient.

14. A wound dressing or implant as set forth in claim 1, wherein said beads have partizle sizes from about 300 to 500 microns.

15. A composition as set forth in claim 1, wherein said beads have particle sizes of from about 300 to 500 microns.

* * * * *

UNITED STATES PATENT AND TRADEMARK OFFICE
CERTIFICATE OF CORRECTION

PATENT NO. : 4,837,285
DATED : June 6, 1989
INVENTOR(S) : Berg et al.

It is certified that error appears in the above-identified patent and that said Letters Patent is hereby corrected as shown below:

On the cover page at (73), delete "Assignee" and replace with --Assignees-- and insert after MediMatrix, Princeton, N.J., --and the University of Medicine and Dentistry of New Jersey, Newark, N.J.--.

Signed and Sealed this

Fifteenth Day of October, 1991

Attest:

Attesting Officer

HARRY F. MANBECK, JR.

Commissioner of Patents and Trademarks